(12) United States Patent
Leeper et al.

(10) Patent No.: US 8,183,177 B1
(45) Date of Patent: *May 22, 2012

(54) SYNERGISTIC COMPOSITION AND METHOD OF USE

(75) Inventors: John R. Leeper, Las Cruces, NM (US); Craig A. Sandoski, Collierville, TN (US)

(73) Assignee: Riceco, LLC, Memphis, TN (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/869,994

(22) Filed: Aug. 27, 2010

(51) Int. Cl.
*A01N 43/40* (2006.01)
(52) U.S. Cl. ......................................... 504/130
(58) Field of Classification Search ................ None
See application file for complete search history.

(56) References Cited

U.S. PATENT DOCUMENTS

| 5,905,060 A | 5/1999 | Fenderson et al. |
| 2003/0203819 A1 | 10/2003 | Sievernich et al. |
| 2011/0098182 A1* | 4/2011 | Mann et al. ................. 504/136 |

FOREIGN PATENT DOCUMENTS

WO  WO 2004-008861 A1  1/2004

OTHER PUBLICATIONS

Norsworthy, J.K. et al., "Herbicide ooptions for rice cutgrass (*Leersia oryzoides*) control", Weed Technology, Mar. 2009, vol. 23, pp. 1-5.
Norsworthy, J.K. et al., "Consultant perspectives on weed management needs in Arkansas rice", Weed Technology, 2007. vol. 21, pp. 832-839.
PCT international search report and the written opinion of the international searching authority or the declaration, May 23, 2011.

* cited by examiner

*Primary Examiner* — Alton Pryor
(74) *Attorney, Agent, or Firm* — Harris, Shelton, Hanover & Walsh

(57) ABSTRACT

The present invention relates to a method to increase the effectiveness of an imidazolinone herbicide to suppress weedy forms of rice growth used with imidazolinone tolerant rice strains. This method involves applying an imidazolinone herbicide to imidazolinone tolerant rice strains in a field and applying a propanil based herbicide to this rice crop, wherein the herbicide includes a herbicidally effective amount a herbicidally active ingredient including propanil and a synergistically effective amount a herbicidally inactive ingredient. The propanil based herbicide synergistically affects the activity of an imidazolinone herbicide by increasing the effectiveness of an imidazolinone herbicide used with the rice to suppress weedy forms of rice growth, such as weedy forms of rice.

5 Claims, 2 Drawing Sheets

US 8,183,177 B1

SYNERGISTIC COMPOSITION AND METHOD OF USE

FIELD OF THE INVENTION

This invention relates to a method to use synergistic combinations, particularly, such combinations for use in controlling weeds in imidazolinone tolerant rice strains.

BACKGROUND OF THE INVENTION

Imidazolinone herbicides are used in a wide range of crops where the crop is tolerant of the imidazolinone and weeds in the crop are susceptible. There are also cases where weeds have become resistant to the imidazolinone herbicides. Rice is naturally susceptible to imidazolinone herbicides. However, resistance was developed within a line of rice that led to commercialization of conventional and hybrid rice varieties currently sold as CLEARFIELD (BASF) rice. NEWPATH (imazethapyr) (BASF) can be sprayed on CLEARFIELD (BASF) rice without injury to the plants. This has become a leading method for controlling weedy forms of rice, a weedy form of rice that is not tolerant of imidazolinone herbicides, in a crop of rice that is tolerant to the imidazolinone herbicide. The imidazolinone sprayed on to CLEARFIELD (BASF) rice also controls other weeds, particularly barnyard grass. NEWPATH (imazethapyr) (BASF) is typically applied at the two- to three-leaf and at the 3-4 leaf stage of weedy forms of rice, such as red rice.

A number of problems, however, have developed with the use of the imidazolinones on CLEARFIELD (BASF) rice. They include: some grass weeds have developed resistance to the imidazolinones and are no longer adequately controlled with the use of the imidazolinones; out crossing of the imidazolinone resistant gene into weedy forms of rice is occurring, making the weedy forms of rice less susceptible to the imidazolinone herbicides; and a portion of the CLEARFIELD (BASF) rice F1 crop is dropped into the field at harvest or due to other factors and can become weedy rice forms with partial tolerance to the imidazolinones in future seasons. Additionally, as the herbicides are sprayed via airplanes some areas of the field may receive less than required amounts of the imidazolinone.

SUMMARY OF THE INVENTION

The present invention relates to a method to increase the effectiveness of an imidazolinone herbicide to suppress weedy forms of rice growth used with imidazolinone tolerant rice strains. This method includes the steps of applying an imidazolinone herbicide to imidazolinone tolerant rice and applying a propanil based herbicide to this rice, wherein the propanil based herbicide includes a herbicidally effective amount of a herbicidally active ingredient including propanil and a synergistically effective amount of a herbicidally inactive ingredient including a carbamate pesticide, to synergistically affect the activity of a imidazolinone herbicide to increase the effectiveness of an imidazolinone herbicide to suppress undesirable weedy forms of rice growth.

The present invention relates to the use of emulsifiers, adjuvant, crop protection chemicals that when applied in combination with the imidazolinone herbicide potentiates or synergizes the imidazolinones herbicidal activity in controlling susceptible and resistant weeds including weedy forms of rice, weedy forms of rice with partial imidazolinone tolerance due to out crossing, and F1 rice that does not possess full tolerance to the imidazolinones.

DETAILED DESCRIPTION OF THE INVENTION

Figure 1:
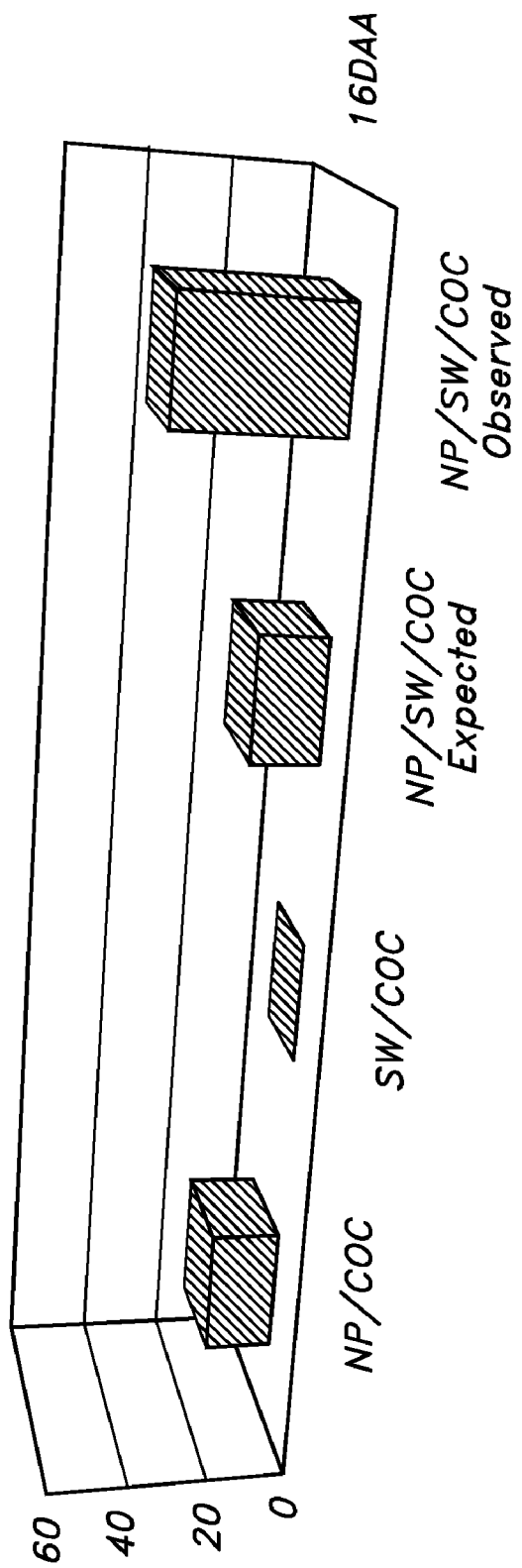
FIG. 1 shows Expected versus Observed Weedy forms of rice Control (%) with NEWPATH (1 oz./A.) and SUPERWHAM! (2.25 qt./A.) with NIS (0.25% v/v) at 16 and 32 DAA. Expected values are based on Colby Method (Weeds 15:20-22). Legend: NP: NEWPATH, NIS: Non-ionic Surfactant, and SW: SUPERWHAM!

This invention relates to a method to use synergistic combinations, particularly, such combinations for use in controlling weeds in imidazolinone tolerant rice strains, such as CLEARFIELD (BASF) rice crops. Imidazolinone herbicides are used in a wide range of crops where the crop is tolerant of the imidazolinone and weeds in the crop are susceptible. For example, imidazolinone herbicides are used to control weedy forms of rice while cultivating imidazolinone tolerant rice strains or rice crops.

This method includes the steps of applying an imidazolinone herbicide to imidazolinone tolerant rice and applying a propanil based herbicide to this rice, wherein the propanil based herbicide includes a herbicidally effective amount of a herbicidally active ingredient including propanil. Other herbicidally effective herbicides can be added to the propanil based herbicide, such as thiobencarb and quinclorac. The term "propanil based herbicide' means that propanil is a required active ingredient in the herbicide. For example, thiobencarb can be mixed or co applied with the propanil based herbicide to synergistically affect the activity of an imidazolinone herbicide. The term "synergistic" means an inhibition or control of weed growth by a combination of chemicals that is greater than would be expected if the chemicals were used individually. This term "synergistic" as used herein is based on formula II from Colby, *Calculating Synergistic and Antagonistic Responses of Herbicidal Combinations*, 15 Weeds 20 (1967) (hereby specifically incorporated by reference in its entirety).

It has been surprisingly found that non-herbicidally active compounds synergistically affect the activity of an imidazolinone herbicide by increasing the effectiveness of an imidazolinone herbicide to suppress weedy forms of rice growth. These herbicidally in-active ingredients include adjuvants that have synergistic effects on imidazolinone herbicide used on imidazolinone tolerant rice strain. In particular, the synergistic effect is such that beneficial effect can be observed after only one application of an imidazolinone herbicide.

An adjuvant is something which is added to a spray solution to increase the effectiveness of the active ingredient. An adjuvant may be packaged and formulated with the herbicide product or they may be added to the spray solution as a tank mix. Surfactants are adjuvants used to increase the dispersing, spreading, wetting, or other properties of the liquids. This term is derived from the words surface active agent. Surfactant molecules are made of two parts: a strong polar group that is attracted to water and a non-polar group attracted to non-aqueous materials, such as oil. Of the types of surfactants, the nonionic surfactants are the most common in agricultural sprays. A crop oil is another common surfactant and is an emulsifiable petroleum-based product that may contain up to 5% surfactants with the remainder being a phytobland oil. A crop oil concentrate (COC) is made of a non-phytotoxic (not causing injury) mineral and/or vegetable oil. A crop oil concentrate contains up to 20% surfactant. The principal function of these materials is to aid in moving the herbicide across the leaf cuticle and reduce the surface tension of the spray droplets. Crop oils are also effective at increasing spray retention on leaf surfaces and reducing drying times. This allows more time for the herbicide to penetrate the leaf.

The inactive portion of the adjuvant can also include an effective amount of nonpolar aromatic hydrocarbon adjuvant (e.g. isophorone, mesitylene oxide and xylene in the finished product formulation) in combination with imidazolinone herbicides that potentiates or synergizes the imidazolinone herbicide activity in controlling susceptible and tolerant weeds including weedy forms of rice, weedy forms of rice, with partial imidazolinone tolerance due to out crossing, and F1 CLEARFIELD (BASF) rice that does not possess full tolerance to the imidazolinones.

The synergistic composition can also include an effective amount of an insecticide, such as SEVIN (carbaryl). Carbamates are organic compounds derived from carbamic acid ($NH_2COOH$). A carbamate group, carbamate ester, and carbamic acids are functional groups that are inter-related structurally and often are interconverted chemically. Carbamate esters are also called urethanes. Carbaryl, the active ingredient in SEVIN (carbaryl) insecticide, belongs to one of the older classes of insecticides called carbamates.

An herbicidal formulation, according to the invention, includes directly sprayable aqueous solutions, suspension concentrates (SC), highly-concentrated aqueous, oily or other suspensions or dispersions, emulsions, oil dispersions, pastes, materials for spreading, which can be applied by means of spraying, atomizing, spreading or pouring. Emulsifiable concentrate (EC) formulations conventionally contain an active ingredient, one or more surfactants which act as emulsifiers upon dilution of the EC with water and a water immiscible solvent. Typical solvents for conventional EC formulations are aromatic hydrocarbons. These solvents have very low solubility in water and a high capability of dissolving a wide range of active ingredients.

Additional suitable inert additives (auxiliaries) include, for example, mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone.

Additionally, imidazolinone herbicides can also be synergized by adjuvants used as spray tank additives (crop oil concentrates, non-ionic surfactants, spreader' stickers). These combinations produce synergistic or unexpected control of weeds in rice when applied at various times, and to rice planted in different ways. To control the weeds, the combination may be applied prior to planting, after planting but prior to flooding (pre-flood, post-emergence rice) or after emergence of the rice and flooding (post-flood, post-emergence rice) and may be applied to either direct seeded (drilled or surface seeded) or transplanted rice.

To be used in combination, it is not necessary that the imidazolinone and the synergistically active chemical or chemicals be applied in a physically combined form, or even at the same time. The combination effect results so long as the imidazolinone and the synergistically active chemical or chemicals are present in or on the targeted foliage of the weeds at the same time in the rice crop, regardless of when they were applied.

Either the imidazolinone and the synergistically active chemical or chemicals could thus be applied in liquid or solid form, or a combination product containing both the imidazolinone and the synergistically active chemical or chemicals could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicides other ingredients such as solvents, wetting agents, suspending agents, anti-caking agents, dispersing agents, emulsifiers, antifreeze agents, antifoam agents, and other additives.

Either the imidazolinone and the synergistically active chemical or chemicals, or both, may be utilized in one of a number of known forms of controlled release compositions. Such compositions provide relatively slow or controlled release of the active ingredient into the environment and include, for example, encapsulations, micro encapsulations, and various forms of controlled release liquid or granules.

Compositions according to this invention may contain the imidazolinone and the synergistically active chemical or chemicals in numerous different physical forms. In some cases, a composition may be produced by simply physically mixing ("tank mixing") commercially available products containing the active ingredients, for example, two emulsifiable concentrates containing the imidazolinone and the synergistically active chemical or chemicals. Alternatively, a package may be manufactured and sold which contains overall the imidazolinone and the synergistically active chemical or chemicals in separate containers, but packaged together, commonly termed a "twin-pack".

Alternatively, previously prepared compositions ("premixes") containing the imidazolinone and the synergistically active chemical or chemicals can be produced. Typical liquid compositions would include an emulsifiable concentrate or suspension concentrate containing the imidazolinone herbicide and other synergistically active chemicals, or a two-phase emulsion (or micro emulsion) with the imidazolinone herbicide is in one phase and the other chemicals are in one or more other phases.

However, a similar solid product containing the imidazolinone and the synergistically active chemical or chemicals could likewise be produced, for instance, as impregnated or extruded granules. Similarly, other solid formulations such as wettable powders or dusts could be prepared.

Again similarly, using appropriate ingredients and conditions, it would be possible to prepare microencapsulated products in which one or both the imidazolinone and the synergistically active chemical or chemicals are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the imidazolinone or the synergistically active chemical or chemicals is contained within the capsules while the other is present in a nonencapsulated form, in the continuous liquid phase. The types of formulations or compositions which may contain the imidazolinone and the synergistically active chemical or chemicals is not limited by those enumerated herein, as other types of formulations would likely be envisaged by those skilled in the art.

Additionally, other biocidally active ingredients or compositions may be combined with the herbicidal compositions of the present invention and used in the methods of the present invention. In addition, the synergistic active ingredients of the present invention can also include insecticides, fungicides, bactericides, acaracides, nematicides, plant growth regulators, fertilizers and plant nutrients, or other herbicides, especially herbicides known to be useful for controlling weeds in a rice crop.

These combinations produced synergistic control of weeds in rice when applied at various times, and to rice planted in different ways. To control the weeds, the synergistic composition may be applied prior to planting, after planting but prior to flooding (pre-flood, post-emergence rice) or after emergence of the rice and flooding (post-flood, post-emergence rice) and may be applied to either direct seeded (drilled or surface seeded) or transplanted rice.

The control of weedy forms of rice weeds by the combination of herbicidal composition including an effective amount of a propanil based herbicide and an effective amount of at least thiobencarb composition to synergistically effect the activity of a imidazolinone herbicide is illustrated by the following examples:

Example 1

NEWPATH 2 SL (imazethapyr) was applied at a rate of 1 oz./acre, a propanil-based herbicide (RICESHOT 4EC (3',4" dichloropropanilide) which is made of 48% propanil active ingredient and 52% inactive ingredients (solvent, emulsifier and adjuvants)), was applied at a rate of 2.25 quart per acre with non-ionic surfactant at a rate of 0.25% v/v. The weedy forms of rice control at 16 days after application (DAA) was observed to be 42.5% with an expected weedy forms of rice control of 7.5% based on Colby's formula (FIG. 1). At 32 days after application, weedy forms of rice control was observed to be 65.2% with an expected weedy forms of rice control of 46.8%. In this combination, synergy was observed because the observed weedy forms of rice control was greater than the expected control. This demonstrates the synergistic effect on weedy forms of rice control of adding an EC formulation of propanil to NEWPATH.

Example 2

Figure 2:
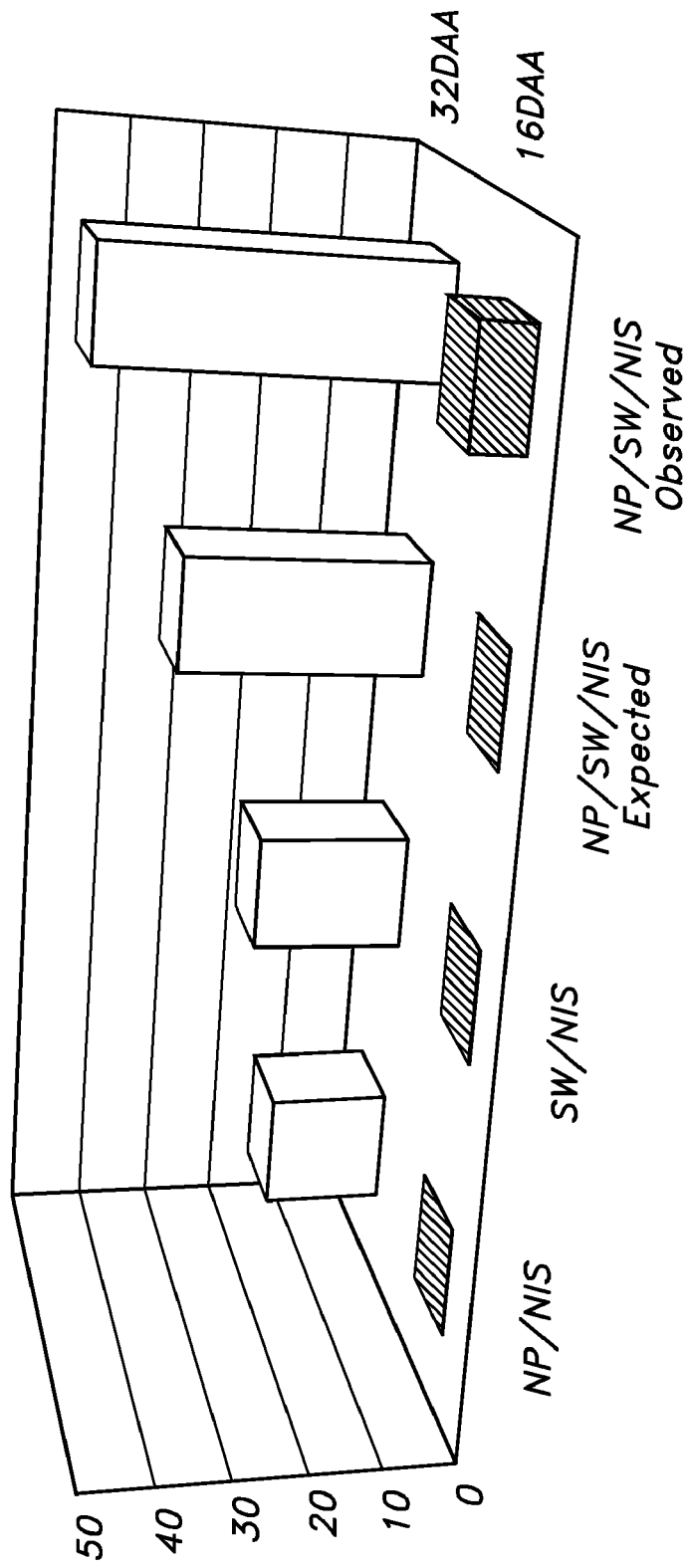
FIG. 2 shows Expected versus Observed Weedy forms of rice Control (%) with NEWPATH (1 oz./A.) and SUPERWHAM! (2.25 qt./A.) with COC (1.0% v/v) at 16 DAA. Expected values are based on Colby Method (Weeds 15:20-22). Legend: NP: NEWPATH, COC: Crop Oil Concentrate, and SW: SUPERWHAM!

NEWPATH 2 SL (imazethapyr) was applied at a rate of 1 oz./acre, a propanil-based herbicide (SUPERWHAM! 4SC (3',4" dichloropropanilide) which is made of 48% propanil active ingredient and 52% inactive ingredients (solvent, emulsifier and adjuvants)), was applied at a rate of 2.25 quart per acre with crop oil concentrate at a rate of 1.0% v/v. The weedy forms of rice control at 16 days after application (DAA) was observed to be 41.7% with an expected weedy forms of rice control of 17.5% based on Colby's formula (FIG. 2). In this combination, synergy was observed because the observed weedy forms of rice control was greater than the expected control. This demonstrates the synergistic effect on weedy forms of rice control of adding an SC formulation of propanil to NEWPATH.

Example 3

NEWPATH (imazethapyr) 2SL is applied at a rate of 1 oz. per acre, a propanil-based herbicide 4EC (3',4" Dichloropropanilide) which is made of 48% active ingredient and 52% inactive ingredient (solvent, emulsifier and other inert ingredients. at a rate of 2.25 qt./A. and NIS (nonionic surfactant IL at a rate of 0.25 percent v/v). The weedy forms of rice control at 16-DAA was 7.5 with an expected red-rice control based on Colby's formula of 0. In this combination synergy was observed because the observed control versus the expected values is different. This shows SC propanil effect. Example 4: NEWPATH (imazethapyr) 2SL is applied at a rate of 1 oz. per acre, Propanil-based Herbicide 4SC (3',4" Dichloropropanilide) which is made of 41.2% active ingredient and 58.8% inactive ingredient (solvent, emulsifier and carbaryl at a rate of 2.25 qt./A. and COC 1 L at a rate of 1 percent v/v. The weedy forms of rice control at 16-DAA was 41.7 with an expected red-rice control based on Colby's formula of 17.5. In this combination synergy was observed because the observed control versus the expected values is different. This shows SC propanil effect.

Example 5

NEWPATH (imazethapyr) 2SL is applied at a rate of 2 oz. per acre, Propanil-based Herbicide 4SC (3',4" Dichloropropanilide) which is made of 41.2% active ingredient and 58.8% inactive ingredient (solvent emulsifier and carbaryl) at a rate of 2.25 qt./A. and NIS (nonionic surfactant) IL at a rate of 0.25 percent v/v. The weedy forms of rice control at 16-DAA was 52.5 with an expected red-rice control based on Colby's formula of 15.0. In this combination synergy was observed because the observed control versus the expected values is different. This shows EC propanil effect.

Example 6

NEWPATH (imazethapyr) 2SL is applied at a rate of 2 oz. per acre, Propanil-based Herbicide 4SC (3',4" Dichloropropanilide) which is made of 41.2% active ingredient and 58.8% inactive ingredient (solvent, emulsifier and carbaryl) at a rate of 2.25 qt/a and COC 1 L at a rate of 1 percent v/v. The weedy forms of rice control at 16-DAA was 61.7 with an expected red-rice control based on Colby's formula of 50.0. In this combination synergy was observed because the observed control versus the expected values is different. This shows the adjuvant effect.

Example 7

NEWPATH (imazethapyr) 2SL is applied at a rate of 2 oz. per acre, Propanil-based Herbicide 4SC (3',4" Dichloropropanilide) which is made of 41.2% active ingredient and 51.2% inactive ingredient (solvent, emulsifier and carbaryl) at a rate of 2.25 qt./A. and TRIPLE PLAY (Agxplore Int.'l) IL at a rate of 12.8 oz./A. TRIPLE PLAY (Agxplore Int'l) is a blend of deposition agents, nonionic surfactants, and activators that enhance the effectiveness of agricultural sprays. The weedy forms of rice control at 16-DAA was 61.7 with an expected red-rice control based on Colby's formula of 57.7. In this combination synergy was observed because the observed control versus the expected values is different. This shows the adjuvant effect.

TABLE 1

| Treatment Number | Treatment | Formulation Strength | Formulation Type | Rate | Units | Rate | Units | Application Timing | Red Rice Control at 16 DAA* | Red Rice Control at 32 DAA* |
|---|---|---|---|---|---|---|---|---|---|---|
| 1 | Superwham | 4 | SC | 5.26 | L/ha% | 2.25 | qt/a% | 2-31frice | 0  h | 21.3 ij |
|   | NIS | 1 | L | 0.25 | v/v | 0.25 | v/v | 2-31frice |  |  |
| 2 | Superwham | 4 | SC | 5.26 | L/ha% | 2.25 | qt/a% | 2-31frice | 0  h | 13.2 j |
|   | COC | 1 | L | 1 | v/v | 1 | v/v | 2-31frice |  |  |
| 3 | Superwham | 4 | SC | 5.26 | L/ha | 2.25 | qt/a | 2-31frice | 12.5 gh | 19.3 ij |
|   | Triple Play | 1 | L | 935 | ml/ha | 12.8 | oz/a | 2-31frice |  |  |
| 4 | Newpath | 2 | SL | 73 | ml/ha | 1 | oz/a | 2-31frice | 7.5 gh | 47.7 gh |
|   | Superwham | 4 | SC | 5.26 | L/ha% | 2.25 | qt/a% | 2-31frice |  |  |
|   | NIS | 1 | L | 0.25 | v/v | 0.25 | v/v | 2-31frice |  |  |
| 5 | Newpath | 2 | SL | 73 | ml/ha | 1 | oz/a | 2-31frice | 41.7 f | 35.7 hi |
|   | Superwham | 4 | SC | 5.26 | L/ha% | 2.25 | qt/a% | 2-31frice |  |  |
|   | COC | 1 | L | 1 | v/v | 1 | v/v | 2-31frice |  |  |
| 6 | Newpath | 2 | SL | 73 | ml/ha | 1 | oz/a | 2-31frice | 50  def | 76.2 b-f |
|   | Superwham | 4 | SC | 5.26 | L/ha | 2.25 | qt/a | 2-31frice |  |  |
|   | Triple Play | 1 | L | 935 | ml/ha | 12.8 | oz/a | 2-31frice |  |  |
| 7 | Newpath | 2 | SL | 146.1 | ml/ha | 2 | oz/a | 2-31frice | 52.5 b-f | 76  b-f |
|   | Superwham | 4 | SC | 5.26 | L/ha% | 2.25 | qt/a% | 2-31frice |  |  |
|   | NIS | 1 | L | 0.25 | v/v | 0.25 | v/v | 2-31frice |  |  |
| 8 | Newpath | 2 | SL | 146.1 | ml/ha | 2 | oz/a | 2-31frice | 61.7 a-d | 93  abc |
|   | Superwham | 4 | SC | 5.26 | L/ha% | 2.25 | qt/a% | 2-31frice |  |  |
|   | COC | 1 | L | 1 | v/v | 1 | v/v | 2-31frice |  |  |
| 9 | Newpath | 2 | SL | 146.1 | ml/ha | 2 | oz/a | 2-31frice | 61.7 a-d | 95.2 ab |
|   | Superwham | 4 | SC | 5.26 | L/ha | 2.25 | qt/a | 2-31frice |  |  |
|   | Triple Play | 1 | L | 935 | ml/ha | 12.8 | oz/a | 2-31frice |  |  |
| LSD (P = .05) |  |  |  |  |  |  |  |  | 16.07 | 19.81 |
| Standard Deviation |  |  |  |  |  |  |  |  | 14.06 | 17.33 |
| CV |  |  |  |  |  |  |  |  | 37.27 | 27.54 |
| Grand Mean |  |  |  |  |  |  |  |  | 37.73 | 62.92 |
| Bartlett's X2 |  |  |  |  |  |  |  |  | 71.679 | 119.439 |
| P(Bartlett's X2) |  |  |  |  |  |  |  |  | 0.001* | 0.001* |
| Replicate F |  |  |  |  |  |  |  |  | 2.779 | 0.281 |
| Replicate Prob(F) |  |  |  |  |  |  |  |  | 0.0195 | 0.9231 |
| Treatment F |  |  |  |  |  |  |  |  | 21.303 | 19.124 |
| Treatment Prob(F) |  |  |  |  |  |  |  |  | 0.0001 | 0.0001 |

*Means followed by the same letter are not significantly different.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claim.

The invention claimed is:

1. A method to increase the effectiveness of imazethapyr to suppress weedy forms of rice growth used with imidazolinone tolerant rice strains comprising:
   applying imazethapyr to said rice; and
   applying a propanil based herbicide to said rice, wherein said propanil based herbicide includes an herbicidally effective amount of an herbicidally active ingredient including propanil and a synergistically effective amount of an herbicidally inactive ingredient including a carbamate pesticide, to synergistically affect the activity of imazethapyr by increasing the effectiveness of imazethapyr used with said rice to suppress weedy forms of rice growth.

2. The method of claim 1 further comprising an effective amount of a non-ionic surfactant to synergistically affect the activity of imazethapyr.

3. The method of claim 1 further comprising an effective amount of an adjuvant to synergistically affect the activity of imazethapyr.

4. The method of claim 1 further comprising an effective amount of an adjuvant to synergistically affect the activity of an adjuvant to solvent.

5. The method of claim 1 further comprising an effective amount of an adjuvant to synergistically affect the activity of a solvent to crop oil concentrate.

* * * * *